United States Patent [19]

Taleisnik

[11] 4,259,752
[45] Apr. 7, 1981

[54] ENDOPROSTHETIC WRIST JOINT

[76] Inventor: Julio Taleisnik, 1201 W. LaVeta #501, Orange, Calif. 92668

[21] Appl. No.: 110,483

[22] Filed: Jan. 4, 1980

[51] Int. Cl.³ .............................................. A61F 1/03
[52] U.S. Cl. .................................... 3/1.91; 128/92 C
[58] Field of Search .................. 3/1.91, 1.9; 128/92 C

[56] References Cited
U.S. PATENT DOCUMENTS

| 4,040,130 | 8/1977 | Laure | 3/1.91 |
| 4,063,314 | 12/1977 | Loda | 3/1.91 |
| 4,106,128 | 8/1978 | Greenwald et al. | 3/1.91 |
| 4,180,871 | 1/1980 | Hamas | 3/1.91 |

Primary Examiner—Clifford D. Crowder
Attorney, Agent, or Firm—Scrivener, Clarke, Scrivener and Johnson

[57] ABSTRACT

This disclosure is of a surgically implantable prosthesis which is particularly intended for use as a replacement for a dysfunctional wrist joint.

3 Claims, 7 Drawing Figures

ENDOPROSTHETIC WRIST JOINT

BACKGROUND OF THE INVENTION

The normal wrist is illustrated in FIG. 3 of the drawings forming part of this specification and comprises three sets of bones: the forearm, the carpals and the metacarpal bones in the hand. The carpals are the bones most closely associated with the motion of the wrist. In the forearm there are two bones, the radius 2 and the ulna 4. In the hand there are eight carpals, which are divided into rows, the proximal and the distal. The proximal row comprises a navicular 6, a lunate (not shown), a triquetrum 8 and a pisiform 10. The distal row comprises a trapezium and a trapezoid 12, a capitate 14 and a hamate. There are five metacarpals consecutively numbered 20 to 24 from the thumb through the last finger.

Wrist movement is divided between the radiocarpal and midcarpal joints of the wrist in a relatively complex manner, displacement of the carpal bones being necessary for motion. The configuration of each row of bones changes according to the position of the hand. Although both joints contribute to all hand motions palmar flexion is predominantly a midcarpal motion and dorsiflexion is radiocarpal. Ulnar deviation also occurs at the radiocarpal joint while radial deviation takes place at the midcarpal level. Anatomical distortion of the carpal bones or loss of integrity of their ligaments or secondary stiffness affects the joint and results in wrist disability.

The carpal bones are held together by ligaments. Collateral ligaments provide lateral support of the wrist, while palmar radiocarpal and dorsal radiocarpal ligaments maintain support of the carpal area. These ligaments define a symmetrical pattern due to insertions into the scaphoid, lunate, triquetrum and capitate bones. It is important that the integrity of the radiocarpal and ulnocarpal bands of ligaments be maintained in carpal bone surgery and that these ligaments not be interferred with or impinged on by the implant.

Currently, there are devices available for either total or partial replacement of the wrist joint. These devices use one or more of the possible types of mechanical articulations available, which are the hinge, ball and socket, or runners in grooves. Most devices use intramedullary stems and acrylic bone cement to secure the prosthesis to bone. Presently available prostheses have components constructed from several types of biologically inactive metals and are designed to articulate with other components constructed from a plastic, such as high density polyethylene.

Several methods or techniques are used to insure that the components remain articulated, and these methods include the use of the soft tissues existent at the time of implantation, the use of pins or screws to hold articular surfaces together, and the use of bayonet type locks. Some types of the available prostheses are quite simple while other types comprise complex mechanical systems, with both types having attendant or inherent disadvantages. The principal disadvantage of the simple prostheses is that they may not reproduce the full range of motion of the joint, while the principal disadvantage of the complex prostheses is the potential complexity of surgery and increased chance of failure, typical causes of such failure including fracture of bone during reaming and breakage of the implant itself. Additionally, the prosthesis components, such as pins, screws or intramedullary stems work loose following implantation. In the event of failure fusion may be required, but such surgery may be difficult if a great deal of bone has been removed.

It has been the principal object of my invention to provide a prosthesis for replacement of the wrist joint having new and improved construction and operative relation of its parts, which will provide maximal motion in dorsiflexion and palmar flexion and ulnar and radial deviation, compatible with satisfactory stability and with possible reproduction of the normal range of wrist motion.

SUMMARY OF THE INVENTION

The endoprosthetic wrist replacement device comprises two components which have means for intramedullary implantation in the radius and a metacarpal bone, respectively. The radial component has a distal head in which there is a distally facing transversely extending groove of generally semi-cylindrical configuration, and the metacarpal component has a proximally located head of generally ovoid shape which is received within the head of the radial component and shaped in the proximal-distal direction to conform to the semi-cylindrical groove and in a transverse direction to permit ulnar and radial deviation.

DESCRIPTION OF THE INVENTION

Figure 1:
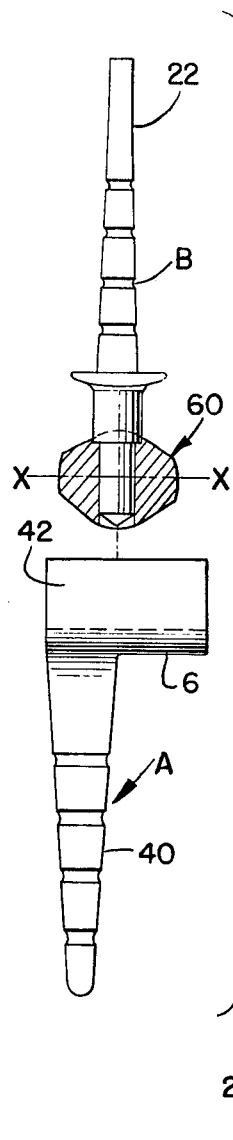
FIG. 1 is an exploded view of the endoprosthetic wrist joint replacement device for the right wrist in neutral anatomical position.
Figure 2:
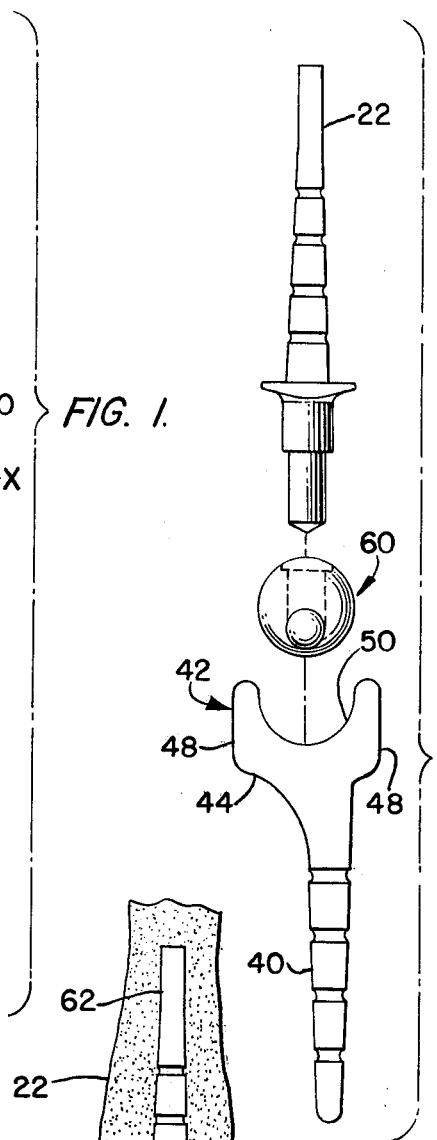
FIG. 2 is an exploded side view of the prosthesis.
Figure 3:
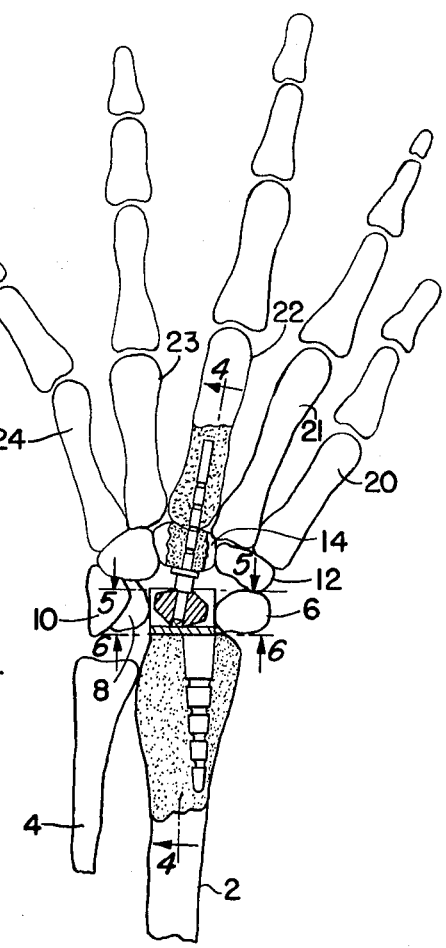
FIG. 3 shows the anatomical bones of a normal left hand viewed from the dorsum with the prosthesis implanted.
Figure 4:
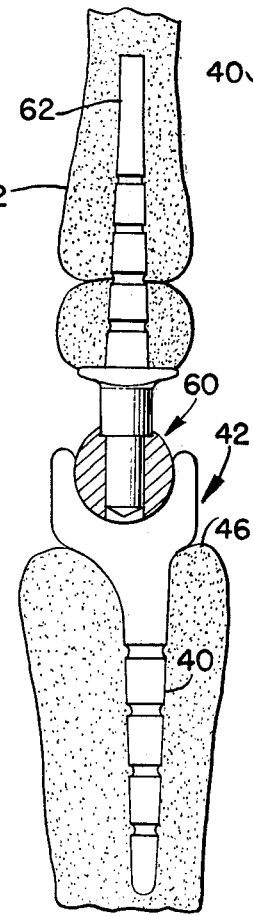
FIG. 4 is a side view of the implanted prosthesis.

The preferred form of the invention is disclosed in this specification, and comprises a radial component A and a carpal-metacarpal component B which are, respectively, adapted and intended to be implanted in the radius and in a distal carpal and a metacarpal bone as illustrated in FIGS. 3 and 4, it being understood that the prosthesis shown in FIG. 1 is constructed and adapted for implantation in the right hand, while FIG. 3 illustrates the prosthesis implanted in a left hand which is viewed from the dorsum.

The radial component A comprises a proximally extending stem 40 for intramedullary implantation formed integrally with a distal socket forming head 42 which has a proximal surface 44 in surface engagement with the prepared distal surface 46 of the radius, side walls 48 which are in volardorsal spaced relation, and an open concave U-shaped distally facing surface 50 which is part-cylindrical in configuration. The head is transversely displaced with respect to the longitudinal axis of the stem in a direction toward the ulna when the prosthesis is implanted, as shown in FIG. 3.

Figures 5, 7:
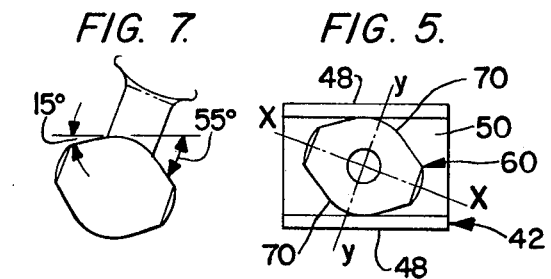
FIGS. 5 and 6 are sectional views taken on lines 5—5 and 6—6 of FIG. 3.
FIGS. 7 and 8 are front views of the head of the metacarpal component of the left hand and right hand prostheses, respectively, viewed from the dorsum.
Figure 8:
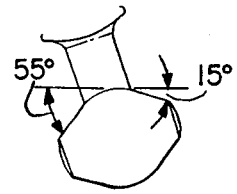
Figure 6:
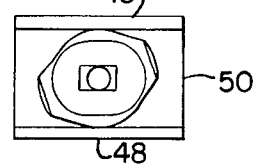

The carpal-metacarpal component B comprises a head 60 which, when the prosthesis is implanted, is proximally positioned to be received within the socket in head 42 of the radial component, and which is integrally formed with a distally extending elongated stem 62 which is constructed for insertion through a carpal bone of the distal row and intramedullary implantation in a metacarpal bone as illustrated in FIGS. 3 and 4. The head 60 is generally ovoid in external configuration with its major axis X—X extending obliquely across the proximal-distal axis of the prosthesis and at an angle to the side walls of the head 42 of the radial component such that when viewed in a proximal-distal direction, it is displaced clockwise for the left wrist and counter clockwise for the right, through an angle of approximately 55° from a position in whch its major axis is parallel to the side walls of the head of the radial component. These angular positions of the head are shown in FIGS. 5 and 6. Because of this angular position of the head the opposite external surfaces 70 along and adjacent the minor axis Y—Y of the head engage the opposite sides of the internal wall of the part-cylindrical surface 50 in the head 42 of the radial component. The head 60 of the metacarpal component is circular in cross-sectional shape along its minor axis Y—Y and has the same external radius as the part-cylindrical surface 50 of the head of the radial component as shown in FIG. 4. In order to permit adequate circumduction the metacarpal component is displaced angularly in a clockwise direction for the left hand, as shown in FIG. 3, and in a counter-clockwise direction for the right hand, and the head 60 is therefore angularly displaced in the designed direction within the head of the radial component. This displacement is shown in FIG. 7 for the left hand prosthesis and in FIG. 8 for the right hand prosthesis, both being viewed in the dorsal-volar aspect.

I claim:

1. An endoprosthesis for implantation to provide an artificial wrist joint, comprising:
    (a) a radial component having an elongated stem for intramedullary implantation in the radius and a distally positioned head integrally formed with the stem, the head having substantially parallel external side walls which are substantially parallel to the axis of the stem, and an internal recess defined by a concave distally facing surface which is part-cylindrical in configuration with its axis parallel to the external side walls and equidistant between them and extending transversely of the proximal-distal axis with a major part of its axial length offset laterally from the axis of the stem in the direction toward the ulna and volarly as well, and
    (b) a metacarpal component having an elongated stem for intramedullary distal implantation in a distal carpal and metacarpal, and a proximal head formed integrally with the stem to be received within the internal recess of the head of the radial component, the head of the metacarpal component being generally ovoid in external configuration and having a circular exterior surface of substantially the same radius as the concave surface of the head of the radial component, and the axis of which is at right angles to the stem and which, when the components are implanted, lies in surface contact with the part-cylindrical surface of the recess in the head of the radial component, and also having a generally oval exterior surface which is positioned about the axis of the stem and engages the side walls of the recess of the head of the radial component.

2. The endoprosthesis according to claim 1, in which the head of the metacarpal component of an implanted left hand prosthesis is displaced angularly in a clockwise direction with respect to the axis of the concave surface of the head of the radial component.

3. The endoprosthesis according to claim 1, in which the head of the metacarpal component of an implanted right hand prosthesis is displaced angularly in a counter-clockwise direction with respect to the axis of the concave surface of the head of the radial component.

* * * * *